United States Patent [19]

Whitlock

[11] 4,421,848

[45] Dec. 20, 1983

[54] METHOD OF DETECTING THE PRESENCE OF LIVE ORGANISMS IN SUBSTANCES

[76] Inventor: Gerald D. Whitlock, Wilton Rd., Malvern, Worcestershire WR14 3RG, England

[21] Appl. No.: 248,847

[22] Filed: Mar. 30, 1981

[30] Foreign Application Priority Data

Apr. 15, 1980 [GB] United Kingdom ............... 8012364

[51] Int. Cl.$^3$ .................. C12M 1/34; C12Q 1/04; C12Q 1/06; C12Q 1/66; C12Q 1/70
[52] U.S. Cl. ........................ 435/8; 435/5; 435/34; 435/39; 435/291
[58] Field of Search ............. 435/8, 27, 28, 31, 34, 435/291, 5, 39, 316, 808

[56] References Cited

U.S. PATENT DOCUMENTS

| 3,564,588 | 2/1971 | Soli | 435/34 |
|---|---|---|---|
| 3,575,811 | 4/1971 | Chappelle et al. | 435/8 |
| 3,933,592 | 1/1976 | Clendenning | 435/34 |
| 3,959,081 | 5/1976 | Witz et al. | 435/34 |
| 4,176,007 | 11/1979 | Frosch et al. | 435/34 |

OTHER PUBLICATIONS

Frobisher, *Fundamentals of Microbiology*, W. B. Saunders Co., Philadelphia, 285-286 (1974).

*Primary Examiner*—Esther M. Kepplinger
*Attorney, Agent, or Firm*—Wigman & Cohen

[57] ABSTRACT

The substance to be tested is premixed by gentle agitation in a glass cuvette with an excess of firefly essence and with a buffer solution and cutting agent, so that any live organisms present are still alive and intact after the mixing has taken place. This gentle agitation is carried out by means of a vibratory tissue disintegrator 11 with the cuvette placed in a container 14 at one end of a reed 13 vibrated by an electromagnet 22. After this the cuvette is violently agitated by the vibratory tissue disintegrator 11 so that the cells are disrupted of any living organisms in the substance, to cause release of about one hundred ATP molecules per cell. Because of the premixing, all or most of the ATP molecules react with the firefly essence almost immediately upon release from the cell, to produce a burst of light which can be distinguished from individual photons produced by stray ATP molecules and from noise within the apparatus.

11 Claims, 1 Drawing Figure

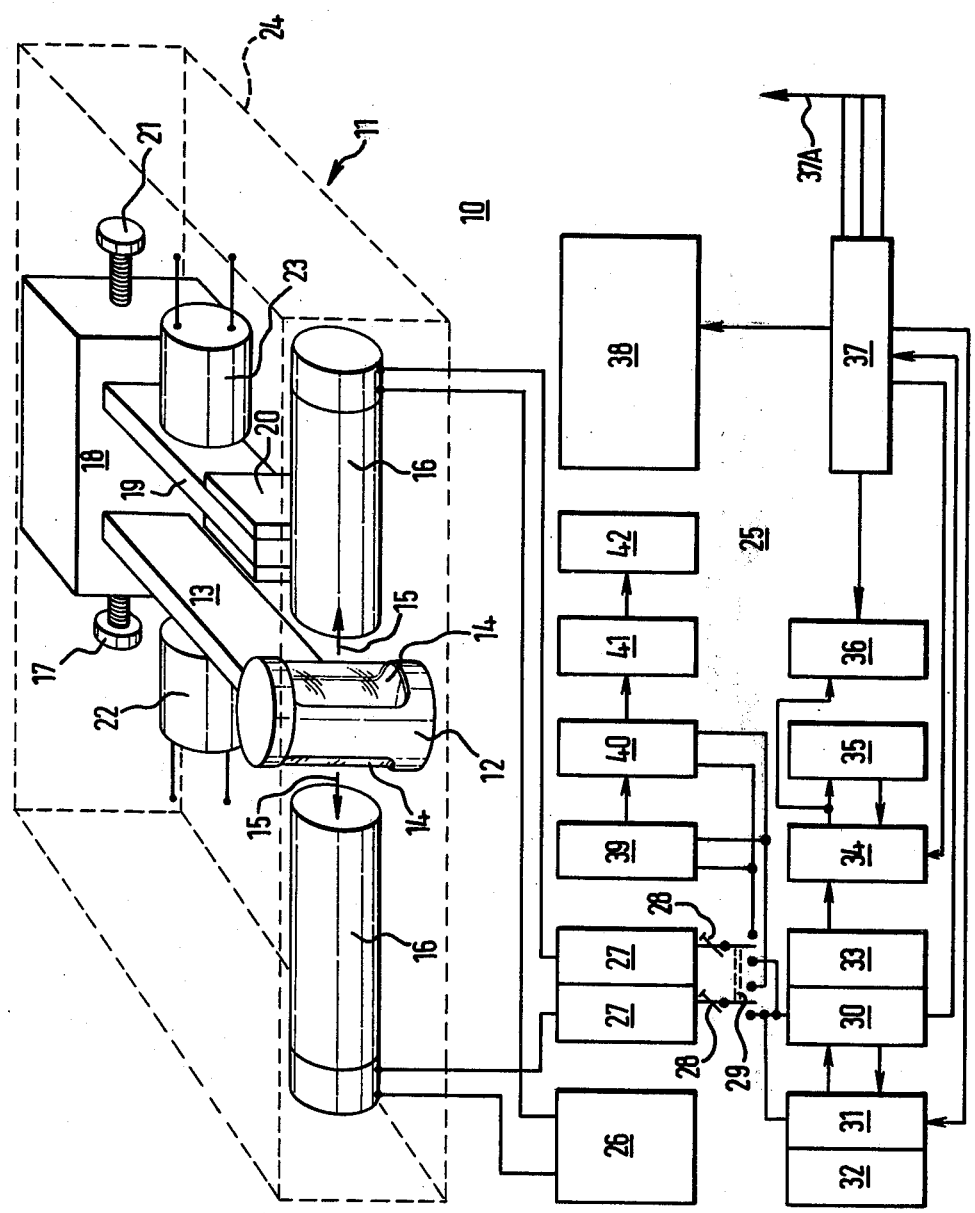

METHOD OF DETECTING THE PRESENCE OF LIVE ORGANISMS IN SUBSTANCES

BACKGROUND OF THE INVENTION

1. Field of the Invention

This invention relates to a method of and apparatus for detecting the presence of live organisms in substances. A particular application of the invention is to the detection of the presence of bacteria or viruses in very small numbers in substances.

2. Description of the Prior Art

It is known that all or most live cells each contain a large number of ATP (andenosine-5′-triphosphate) molecules, many or all of which molecules are released if the cell is disrupted, that is to say, the outer cell membrane ruptured and the cell contents dispersed. (ATP molecules in dead cells are quickly broken down by autolysis.) It is also known that when ATP molecules react with firefly essence (i.e. "Luciferin" reagent and "Luciferase" enzyme) photons of light are produced according to the following formula:

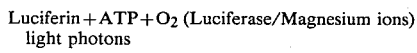
Luciferin + ATP + O$_2$ (Luciferase/Magnesium ions) light photons

That is to say, the andenosine-5′-triphosphate ("ATP") molecules react with the reagent Luciferin in the presence of oxygen and magnesium ions and the Luciferase enzyme to produce light photons, one photon per ATP molecule. A living cell may contain approximately 100 ATP molecules. Reference may be made to an article entitled "The energy source for bioluminescence in an isolated system" by W. D. McElroy in Volume 33 (1974) page 342–345 of the Proceedings of the National Academy of Science and to another article entitled "Luminometry - a sensitive technique in analytical chemistry and medical sciences" by S. Kolehmainen at pages 129–135 of the September/October 1979 issue of "International Laboratory".

Even a single light photon can be detected by a suitably positioned photo-multiplier (PM) to produce an electric pulse output. However the PM has to be highly sensitive for this purpose, rendering the PM liable to produce electric pulse outputs in response to spurious disturbances as "noise". Furthermore, impurity ATP molecules react with the firefly essence to produce photons of light.

It is also known that a bacterium cell (and possibly even a virus) can be ruptured (or burst open) by violent agitation alone (e.g. ultrasonically) or with a cutting agent (if not ultrasonically) such as aluminium oxide, ballotini beads, sand or carborundum, in water.

SUMMARY OF THE INVENTION

The invention is based upon or stems from realisation or discovery of the fact that the act of disrupting a live cell (e.g. a bacterium or virus) can be arranged to produce a "burst" of photons (i.e. a substantial number of photons in a short period of time) if the live cell is already in intimate contact with a substantial amount of firefly essence at the instant of disruption, so that all or substantially all of the ATP molecules which are released when the cell is disrupted react almost immediately with firefly essence to produce respective photons of light. However, the inventive method and apparatus need not be limited to the reaction of ATP molecules with firefly essence.

According to a first aspect of the invention there is provided a method of detecting the presence of live organisms in a substance, comprising the steps of causing said live organisms to produce bursts of light photons by being suddenly disrupted in the presence of a light-photon-producing reagent and detecting said bursts of light photons.

According to a second aspect of the invention there is provided a method of detecting the presence of live organisms in a substance, comprising the steps of disrupting said organisms by treatment of the substance so that certain constituents of said organisms are released, bringing said constituents into close relationship with a light-photon-producing reagent so that photons of light are produced and detecting said photons of light, characterised in that said organisms are already in close relationship with said reagent when they become disrupted so that each disruption of a live organism causes production of a burst of light photons.

According to a third aspect of the invention there is provided a method of detecting the presence of live organisms in a substance comprising the steps of: treatment of the substance in such a way that all or most of the live organisms are disrupted; mixing the substance with a reagent adapted to cause the production of light photons upon contact with certain constituents of disrupted live organisms; and detecting said light photons; characterised in that said mixing of the substance with the reagent is carried out prior to said treatment of the substance so that the live organisms while still intact come into intimate contact with the reagent, and in that a disrupting agent which is ineffective until said treatment occurs is mixed with the substance and with the reagent prior to said treatment of the substance.

According to a fourth aspect of the invention there is provided apparatus for detecting the presence of live organisms in a substance, comprising a substantially transparent receptacle into which can be put the substance and a light-photon-producing reagent, a light-tight chamber for occupancy by the receptacle, means for mixing the substance and the reagent inside the receptacle, without disrupting substantially any live cells, means for disrupting any live cells in the mixture of the substance and reagent in the receptacle inside the light-tight chamber so as to produce a burst of photons, and means for detecting photons inside the chamber and producing a corresponding electrical output distinguishing the burst of photons from spurious photons and background noise.

The invention will be described by way of example with reference to the accompanying drawing.

BRIEF DESCRIPTION OF THE DRAWING

The drawing illustrates an apparatus embodying the fourth aspect of the invention and adapted for use in a method in accordance with the first, second and third aspects of the invention.

DESCRIPTION OF THE PREFERRED EMBODIMENT

Referring to the drawing, the illustrated apparatus 10 comprises a high speed vibratory tissue-disintegrator 11 which is a modification of one manufactured by Mickle Laboratory Engineering Co. Ltd. of Mill Works, Gomshall, Near Guildford, Surrey, England.

The tissue-disintegrator 11 comprises a single screw-capped metal container 12, for a transparent glass cuvette containing the substance being tested, mounted at an outer end of a vibratory reed 13. The container 12 has two window openings 14 facing along its axis 15 of vibration, that is to say, at right angles to the "plane" of the reed 13, for detection of photons of light inside the cuvette (which is faintly visible through one window opening 14) by two photomultipliers 16 which are mounted respectively opposite the two window openings 14. The other, inner, end of the reed 13 is clamped by a screw 17 to a firmly mounted base 18. Upon loosening the screw 17, the effective length of the reed 13 can be altered by pushing it into or pulling it out of the base 18. The container 12 and reed 13 are counterbalanced relative to the base 18 when vibrating by a second reed 19 carrying counterweights 20 and clamped to the base 18 by a second screw 21, upon loosening which the effective length of reed 19 can be varied, analogously to the reed 13. Two electromagnets 22 and 23 are fixedly mounted (by means not shown) adjacent intermediate portions of reeds 13 and 19 respectively and are energisable by alternating or pulsating electric current to vibrate the reeds 13 and 19 respectively. Finally, the tissue-disintegrator 11 comprises a light-tight box 24, indicated by broken lines, containing items 12 to 23, so that the only light to reach photomultipliers 16 is that from inside the cuvette in operation as described hereinafter.

The apparatus 10 also comprises electronic circuitry 25 for processing the outputs from the photomultipliers 16 (and for controlling the vibration of reeds 13 and 19 and hence of container 12).

The electronic circuitry 25 comprises the following components: a high voltage source 26 connected to the two photomultipliers 16 as shown to supply them with high voltage; two amplifiers 27 respectively connected to the outputs of the two photomultipliers 16 as shown to amplify their respective outputs; two adjustable signal attenuators 28 connected to the outputs of the two amplifiers 27 to adjustably attenuate their outputs for, inter alia, the purpose of distinguishing between genuine signals and noise; (these may be replaced by threshold devices such as zener diodes, not shown); and a two-gang, two-pole changeover switch 29 connected to the outputs of attenuators 28. For a preferred mode of operation, the electronic circuitry 25 also comprises: a fast counter 30 for cumulatively counting output pulses from the two attenuators 28 (or the alternative threshold devices mentioned above); a fast timer 31 for timing a selected short interval, of the order of, for example, one millisecond, from the arrival of a pulse at counter 30 when counter 30 is at zero, and for resetting counter 30 to zero at the end of said short interval; an interval selector 32 for selecting the short interval to be timed by timer 31; a count selector 33 for selecting a minimum count of counter 30 (in the short interval timed by timer 31) to produce an "event" pulse to pass via selector 33 from counter 30 to an event counter 34; a "slow" timer 35 for timing a interval for the event counter 34, for determining the number of "events" in this interval of time (and then optionally resetting counter 34 to zero); and a display unit 36 for displaying the number of events counted by counter 34. A "chemiluminescence delay ratemeter" 37 controls, via outputs indicated schematically at 37A, the energisation of electromagnets 22 and 23 and hence the vibration of container 12, to produce selectively nil agitation, gentle agitation and violent agitation of the cuvette. The chemiluminescence delay ratemeter 37 (referred to as the "ratemeter 37" for brevity) receives an input from counter 30, whereby abnormally high counts during gentle agitation, or even no agitation, can be detected. At this point it is apposite to explain that the gentle agitation is intended to produce good mixing of the substance and the reagent but without disruption of any live cells, so that abnormally high counts would normally be due to impurities in the reagent or even in the substance.

Accordingly the ratemeter 37 is responsive to abnormally high counts during no agitation or gentle agitation respectively to delay commencement of gentle agitation or violent agitation until the counts have subsided to a normal level. Ratemeter 37 is connected to a recorder 38 for recording results of tests.

For an alternative mode of operation, the electronic circuitry 25 also comprises: a coincidence detector 39 for detecting simultaneous or substantially simultaneous output pulses from the two attenuators 28 (or the alternative threshold devices mentioned above); a summation amplifier 40 for summing the pulses detected as coincident by detector 39; a counter display 41 for displaying the result; and a timer 42 whose function is analogous to that of timer 35.

In use, in for example a test for the presence of any living cells in a substance, a sample of the substance is put into a transparent cuvette of known type. Also put into the cuvette is firefly essence (i.e. Luciferin and Luciferase) in substantial excess, an aqueous buffer solution (for the oxygen and magnesium ions) and a cutting agent such as aluminium oxide. The cuvette is then placed in the container 12. The lengths of the arms 13 and 19 will already have been adjusted for resonant vibration at the frequency of the supply voltage. Then, with switch 29 set to connect attenuators 28 (or the alternative threshold devices mentioned above) to counter 30, with interval selector 32 set at about one millisecond, and count selector 33 set at five (that is, a count of five pulses in counter 30 in the one millisecond interval set by selector 32 to constitute an "event") the apparatus is switched on. Initially there is no vibration of container 12. If it should happen that stray ATP molecules and other "noise" factors cumulatively are producing an abnormally high pulse rate from counter 30 (that is, substantially higher than the normal rate of, say, one per millisecond on average, the ratemeter 37 indicates this and postpones the onset of agitation of the container 12. When the pulse rate from counter 30 has fallen to a normal level, which happens when the stray ATP molecules have nearly all reacted with the firefly essence, the ratemeter 37 switches on a low voltage supply to electromagnets 22 and 23 for gentle agitation of the cuvette in container 12, to achieve thorough pre-mixing without (substantial) disruption of any live cells therein. This gentle agitation is carried out until stray ATP molecules and other noise factors, introduced as a consequence of gentle agitation, cumulatively are producing a normal pulse rate from counter 30 as determined by the ratemeter 37, after which the ratemeter 37 switches the energisation of electromagnets 22 and 23 from low to high voltage and starts timer 36. The high voltage causes violent agitation of the cuvette so that the cutting agent disrupts or bursts open any live cells in the mixture, releasing ATP molecules which quickly encounter and react with the firefly essence (which is there in excess) to produce a burst or bursts of light photons which are detected by the photomultipliers 16. It may be assumed that, given the fact that approximately one hundred ATP molecules are released when a live cell is disrupted, there will be a certain time spread in the production of the photons, instead of all the photons being produced simultaneously, so that at least, say, five distinct pulses will be produced by counter 30 in response to at least five distinct photons or groups of photons, for "event counter" 34 to count an "event", namely, the disruption (and thus the presence) of a live cell, (live, that is, until killed by the violent agitation in the conditions set out above). The number of "events" indicated on display unit 36 is equal to, or at least indicative of, the number of live cells present in the sample in the cuvette (not shown) in container 12 before the apparatus was switched on.

The following comments may be made about the above-described apparatus and method:

(i) The ability of ratemeter 37 to delay the onset of violent agitation (and even the onset of gentle agitation) if the pulse rate is abnormally high during gentle agitation (or during no agitation respectively) allows impurity ATP molecules to react with the Firefly essence before measurements start, so as not to effect the measurements themselves. Hence it is possible to use poor quality reagents containing impurity ATP or possible to test samples containing impurity ATP molecules;

(ii) Because the cells are already intimately mixed with the firefly essence when they become disrupted, the ATP molecules and the firefly essence react together almost immediately;

(iii) Because violent agitation is taking place during cell disruption, the ATP molecules can come into contact with fresh firefly essence very quickly, even if the firefly essence in the immediate vicinity of the cell at the time of disruption is exhausted by reaction with other ATP molecules;

(iv) The arrangement is designed to give the maximum light output in the shortest possible time for each disruption of a living organism cell;

(v) The essence of the method is that by keeping the living organism cells intact in the cuvette until after they have been mixed with an excess of firefly essence, and then rupturing the cells in the presence of the excessive firefly essence, the light produced by the cloud of ATP molecules reacting with the firefly essence appears as a burst of light, related to the time of rupturing, these bursts of light being detected electronically as "events";

(vi) This method permits the detection of a very small number of living organism cells, namely, approximately ten per milliliter, in a very short time, in fact, less than ten seconds;

(vii) Very little preparation of each sample is required, so that there is the possibility of further development of the invention to incorporate an automatic sample charger for the purpose of sequential automatic testing of a number of different samples;

(viii) The choice of one millisecond for the fast timer 31 and a count of five for the count selector 33 is based on estimation of the probability that a count of five photon-produced pulses in one millisecond is unlikely except in the event of rupture of a living organism cell. It is possible that certain substances and/or certain qualities of firefly essence will require modification of these settings.

For the alternative mode of operation mentioned above, using items 39 to 42 of the electronic circuitry 25, with switch 29 switched over to connect the attenuators 28 (or the alternative threshold devices mentioned above) to coincidence detector 39 and summation amplifier 40, the method relies upon the probability that only rupture of a living organism cell will produce sufficient light to cause production substantially simultaneously of output pulses from both photomultipliers 16.

It is conceivable that some other method, such as ultrasonic agitation, might be used for rupturing the cells, instead of the vibratory tissue disintegrator 11.

Furthermore, it may be deemed desirable to cool the cuvette or to maintain a constant temperature of the cuvette during measurement, and/or to do likewise with the photomultipliers 16.

It may be desirable to repeat the measurement after a period of incubation to allow cell multiplication in the cuvette.

It may be desirable to add nutrient media, and/or other reagents and chemicals to the mixture in the cuvette, prior to measurement.

Other light detecting devices besides photomultipliers, for example, silicone photodiodes, may be used.

Furthermore, in the preferred mode of operation, it is possible that a single light detector (whether photomultiplier or other) may be sufficient, or that more than two light detectors may be desirable.

It is possible that light losses due to absorption, low photon detection efficiency of the light detectors, excessive photon production by impurity ATP molecules, and electronic noise during the actual cell measurement, may require a much higher setting of the count selector 33, such that substantially simultaneous disruption of two, three or even more living organism cells is necessary for an "event" to be detected.

I claim:

1. A method of detecting the presence of live organisms in a substance, comprising the steps of gently and completely mixing said live organisms with a light-photon-producing reagent which is capable of producing photons when contacted with ATP and then violently agitating the mixture to cause each organism to be disrupted, release ATP and produce a burst of light photons and detecting the bursts of light photons said reagent being present in an amount sufficient to allow substantially all ATP upon release to react almost immediately with said reagent.

2. In a method of detecting the presence of live organisms in a substance employing the steps of disrupting said organisms by treatment of the substance so that certain constituents of said organisms are released, bringing said constituents into close relationship with a light-photon-producing reagent so that photons of light are produced and detecting said photons of light, the improvement comprising the steps of: gently and completely mixing said organisms with said reagent prior to said organisms becoming suddenly disrupted by violent agitation so that each disruption of a live organism causes production of a burst of light photons and detecting the bursts of light photons.

3. In a method of detecting the presence of live organisms in a substance wherein treatment of the substance is carried out in such a way that all or most of the live organisms are disrupted to release certain constituents; the substance is mixed with a reagent adapted to cause the production of light photons upon contact with said constituents of disrupted live organisms; and said light photons are detected; the improvement comprising the steps of: gently and completely mixing the substance with the reagent in an amount sufficient to allow substantially all of said constituents upon release to react almost immediately with said reagent prior to said treatment of the substance so that the live organisms while still intact come into intimate contact with the reagent, and employing a disrupting agent which is ineffective until said treatment occurs, said disrupting agent being mixed with the substance and with the reagent prior to said treatment of the substance and wherein said treatment comprises violently agitating said organisms to disrupt them, release the constituents and produce a burst of light photons.

4. A method as claimed in claim 3 wherein said reagent is firefly essence.

5. A method as claimed in claim 3 wherein the disruption is caused by violent agitation with a disrupting agent.

6. A method as claimed in claim 5 wherein the disrupting agent is selected from the group consisting of aluminium oxide, ballotini beads, sand and carborundum.

7. A method as claimed in claim 3 wherein each detected photon produces an electrical pulse output from a photon detector.

8. A method as claimed in claim 7 wherein a timed period is commenced in response to an electrical pulse from the photon detector and the number of electrical output pulses from the detector in the timed period is counted by a fast counter, to be recorded as a single event in a slow counter if said number exceeds a threshold value.

9. A method as claimed in claim 3 wherein spurious signal outputs due to "noise" and impurity ATP are distinguished from a burst of photons produced upon disruption of a live cell or number of cells by counting the photons detected in a short timed period commencing with an initial detected photon, and recording the count as one disrupted live cell or number of cells if the count is above a predetermined minimum.

10. A method as claimed in claim 3 wherein a plurality of spatially distributed detectors are used to detect photons and wherein only substantially simultaneous outputs from all or at least some of said detectors are counted as a disrupted live cell.

11. In a method of detecting the presence of live organisms in a substance comprising the steps of: treatment of the substance in such a way that all or most of the live organisms are disrupted; mixing the substance with a reagent adapted to cause the production of light photons upon contact with certain constituents of disrupted live organisms; and detecting said light photons; the improvement comprising the steps of mixing the substance with a firefly essence reagent in an amount sufficient to allow substantially all of said constituents upon release to react almost immediately with said reagent prior to said treatment of the substance so that the live organisms while still intact come into intimate contact with the reagent, and that a disrupting agent which is ineffective until said treatment occurs is mixed with the substance and with the reagent prior to said treatment of the substance.

* * * * *